(12) United States Patent
Sheng et al.

(10) Patent No.: US 10,899,767 B2
(45) Date of Patent: Jan. 26, 2021

(54) CRYSTAL FORM OF ACP-196, PREPARATION METHOD THEREFOR AND PHARMACEUTICAL COMPOSITION THEREOF

(71) Applicant: Hangzhou SoliPharma Co., Ltd., Zhejiang (CN)

(72) Inventors: Xiaohong Sheng, Zhejiang (CN); Xiaoxia Sheng, Zhejiang (CN); Tao Zhu, Zhejiang (CN)

(73) Assignee: Hangzhou SoliPharma Co., Ltd., Zhejiang (CN)

( * ) Notice: Subject to any disclaimer, the term of this patent is extended or adjusted under 35 U.S.C. 154(b) by 0 days.

(21) Appl. No.: 16/339,728

(22) PCT Filed: Oct. 5, 2016

(86) PCT No.: PCT/CN2016/101430
§ 371 (c)(1),
(2) Date: Apr. 5, 2019

(87) PCT Pub. No.: WO2018/064797
PCT Pub. Date: Apr. 12, 2018

(65) Prior Publication Data
US 2019/0382405 A1    Dec. 19, 2019

(51) Int. Cl.
*C07D 487/04* (2006.01)
*A61K 31/4985* (2006.01)
*A61P 19/02* (2006.01)

(52) U.S. Cl.
CPC ........ *C07D 487/04* (2013.01); *A61K 31/4985* (2013.01); *A61P 19/02* (2018.01); *C07B 2200/13* (2013.01)

(58) Field of Classification Search
CPC .... C07D 487/04; A61K 31/4985; A61P 19/02
USPC ......................................... 544/350; 514/259
See application file for complete search history.

(56) References Cited

U.S. PATENT DOCUMENTS 9,796,721 B2 * 10/2017 Blatter ................... A61K 45/06

FOREIGN PATENT DOCUMENTS

| WO | WO-03084949 A1 | 10/2003 |
| WO | WO-2013010868 A1 | 1/2013 |
| WO | WO-2014071109 A1 | 5/2014 |
| WO | WO-2015110923 A2 | 7/2015 |
| WO | WO-2015181633 A2 | 12/2015 |
| WO | WO-2015185998 A2 | 12/2015 |
| WO | WO-2018064797 A1 | 4/2018 |

OTHER PUBLICATIONS

Whang et al., Drug Discovery Today, pp. 1-5, 2014.*
Akinleye et al. Journal of Hematology & Oncology 2013, 6:59.*
Chakravarty et al. Clinical Immunology (2013) 148, 66-78.*
Norman P. Expert Opinion on Investigational Drugs, 25:8, 891-899,2016.*
International Search Report and Written Opinion for International Application No. PCT/CN2016/101430, Intellectual Property office of the P.R. China, China, dated Jun. 30, 2017, 18 pages.
Braga, D., et al., "Crystal Polymorphism and Multiple Crystal Forms", Struct Bond (132): 25-50, Springer-Verlag Berlin Heidelberg, Germany (2009).

* cited by examiner

*Primary Examiner* — Venkataraman Balasubramanian
(74) *Attorney, Agent, or Firm* — Sterne, Kessler, Goldstein & Fox P.L.L.C.

(57) ABSTRACT

Crystalline forms of ACP-196, preparation methods, pharmaceutical compositions and uses thereof in the preparation of drugs for treatment and/or prevention of Bruton's tyrosine kinase (BTK)-mediated disorders such as autoimmune diseases or disorders, heteroimmune diseases or disorders, cancers including lymphoma and inflammatory diseases or disorders. As compared with the known solid form of ACP-196, the crystalline forms of the present invention have advantages in crystallinity.

7 Claims, 7 Drawing Sheets

CRYSTAL FORM OF ACP-196, PREPARATION METHOD THEREFOR AND PHARMACEUTICAL COMPOSITION THEREOF

FIELD OF THE INVENTION

The present invention relates to the technical field of crystallization in pharmaceutical chemistry. Specifically, the present invention relates to novel crystalline forms of ACP-196, preparation methods and pharmaceutical compositions and uses thereof.

BACKGROUND

ACP-196 is a second-generation Bruton's tyrosine kinase (BTK) inhibitor that can be used to treat or prevent Bruton's tyrosine kinase-mediated diseases and symptoms such as chronic lymphocytic leukemia (CLL). The drug works by permanently binding to BTK. BTK is part of a chain of protein chains that transmit growth signals from the surface of CLL cells to genes in the nucleus, causing cancer cells to survive and grow. By blocking BTK, ACP-196 can stop the transmission of this growth signals and thus CLL cells die.

ACP-196, has the chemical name of 4-[8-amino-3-[(2S)-(1-(1-oxo-2-butyn-1-yl)-2-pyrrolidinyl]imidazo[1,5-a]pyrazin-1-yl]-N-2-pyridinebenzamide, and its English name is acalabrutinib, with CAS No. 1420477-60-6. The chemical structure of ACP-196 is shown in the following formula (II).

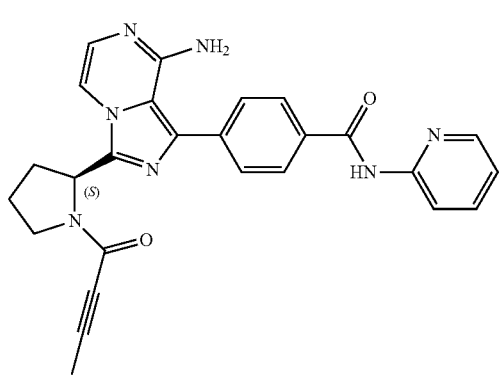

(II)

Patent Document CN103889987A reported the preparation of ACP-196 and disclosed liquid chromatography mass spectrometry (LCMS) data of ACP-196. The present inventors have found that ACP-196 obtained according to the preparation method in Example 6 of CN103889987A is a yellow amorphous material which has the disadvantages including solid form instability, susceptible to moisture absorption, and poor flowability. Patent document CN103889987A also mentioned that physical forms such as amorphous form and various crystalline forms are within the scope of protection thereof, but the patent does not provide characteristic data of any of these physical forms and therefore cannot be treated as fully disclosed.

In view of the disadvantages in the prior art, it is necessary to develop new solid forms of ACP-196 with more advantageous properties to meet the strict requirements in pharmaceutical formulations on morphology, stability and other physicochemical properties of active substances.

SUMMARY OF THE INVENTION

According to the defects of the prior art, the purpose of the present invention is mainly to provide new crystalline forms of ACP-196, and their preparation methods, pharmaceutical compositions and uses thereof. The crystalline forms should be stable crystalline solids with one or more improved properties, especially in the aspects of crystallinity, hygroscopicity, morphology, formulaion processability and solid-state form stability.

According to the purpose of the invention, the first aspect of the invention is to provide a solid-state ACP-196 Form 1 and its preparation method.

The present invention provides ACP-196 Form 1 with its structure shown in the formula (I) below:

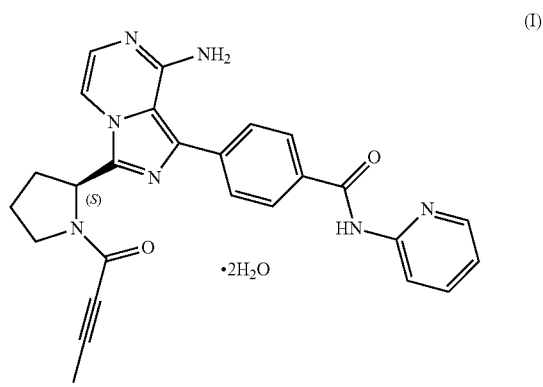

(I)

ACP-196 Form 1 is a dihydrate, using Cu-Kα radiation, the X-ray powder diffraction pattern of ACP-196 Form 1, expressed as 2θ angles, has the following characteristic peaks: 7.6±0.2°, 10.5±0.2°, 12.6±0.2°, 15.2±0.2°, 17.9±0.2° and 21.7±0.2°.

In a preferred embodiment of the present invention, the X-ray powder diffraction pattern of ACP-196 Form 1, expressed as 2θ angles, has the following characteristic peaks: 7.6±0.2°, 10.5±0.2°, 12.6±0.2°, 14.1±0.2°, 14.6±0.2°, 15.2±0.2°, 17.9±0.2°, 21.7±0.2°, 23.1±0.2°, 24.2±0.2°, 25.2±0.2° and 27.0±0.2°.

In a further preferred embodiment of the present invention, the X-ray powder diffraction pattern of ACP-196 Form 1, expressed as 2θ angles, has the following characteristic peaks and relative intensities:

| Diffraction angel 2θ | Relative intensity % |
|---|---|
| 7.6 ± 0.2° | 12.3 |
| 10.5 ± 0 2° | 38.5 |
| 12.6 ± 0.2° | 100.0 |
| 14.1 ± 0.2° | 22.2 |
| 14.6 ± 0.2° | 27.2 |
| 15.2 ± 0.2° | 34.1 |
| 17.9 ± 0.2° | 76.3 |
| 21.0 ± 0.2° | 15.1 |
| 21.3 ± 0.2° | 18.8 |
| 21.7 ± 0.2° | 51.7 |
| 22.6 ± 0.2° | 13.4 |
| 23.1 ± 0.2° | 72.4 |
| 24.2 ± 0.2° | 32.3 |
| 24.5 ± 0.2° | 26.1 |
| 24.8 ± 0.2° | 31.7 |
| 25.2 ± 0.2° | 33.2 |
| 27.0 ± 0.2° | 24.8 |
| 28.4 ± 0.2° | 12.5 |

Non-restrictively, in one typical embodiment of the present invention, the X-ray powder diffraction pattern of ACP-196 Form 1 is shown in FIG. 5.

Non-restrictively, the TGA thermogram of ACP-196 Form 1 is shown in FIG. 6.

Non-restrictively, the PLM plot of ACP-196 Form 1 is shown in FIG. 7.

Non-restrictively, the isothermal sorption plot of ACP-196 Form 1 is shown in FIG. 8.

Compared with the known amorphous ACP-196, ACP-196 Form 1 has the following beneficial properties:

1) According to the XRPD pattern and PLM plot, ACP-196 Form 1 is a crystalline solid with high crystallinity and good morphology.

2) According to the isothermal sorption plot, the weight change of ACP-196 Form 1 is 0.8% between 30 to 80% RH, while the weight change of amorphous ACP-196 in the same humidity range is 5.5%. ACP-196 Form 1 is less hygroscopic.

The above advantageous properties of ACP-196 Form 1 show that, compared with the known amorphous ACP-196, ACP-196 Form 1 has many advantages and is more suitable for being used as the solid form of the active ingredient in pharmaceutical formulations. The amorphous material is unstable and it is prone to crystallize under the influences of environmental factors such as temperature and humidity. Such instability may further affect the quality and stability of the pharmaceutical formulations. ACP-196 Form 1 is crystalline, and its solid form stability is obviously better (than that of amorphous solids). Crystalline solids usually have better flowability and processing (such as filtrating, drying, weighing, screening, etc) characteristics, which are beneficial in improving the homogeneity of active ingredients and pharmaceutical formulations. In addition, ACP-196 Form 1 has lower hygroscopicity, which may better ensure the quality of the active ingredients and formulations containing ACP-196 Form 1, avoiding and reducing quality issues, safety issues and stability issues during pharmaceutical production and/or storage, such as content uniformity and impurity issues, avoiding special and expensive package.

The present invention provides preparation methods of ACP-196 Form 1, which comprise any one of the following preparation methods:

1) Forming a suspension of ACP-196 solids in a solvent, stirring for crystallization and precipitation, and then separating and drying to obtain ACP-196 Form 1;

preferably, the solvent is selected from the group consisting of alcohols mixed with water, ketones mixed with water, tetrahydrofuran mixed with water, 1,4-dioxane mixed with water and acetonitrile mixed with water, more preferably acetonitrile and water mixture;

preferably, the volume percentage of water in the solvent is from 50% to 100%, more preferably from 75% to 80%;

preferably, the weight to volume ratio of ACP-196 solids to solvent is from 25 mg/1 mL to 100 mg/1 mL;

preferably, the stirring time is from 1 day to 7 days, more preferably from 3 days to 7 days;

preferably, the stirring is carried out at 25° C. to 40° C.

2) Forming a solution of ACP-196 solids in a co-solvent, adding anti-solvent, stirring for crystallization and precipitation, and then separating and drying to obtain ACP-196 Form 1;

preferably, the co-solvent is selected from the group consisting of alcohols, ketones, tetrahydrofuran, 1,4-dioxane, acetonitrile and dimethyl sulfoxide, more preferably ethanol or dimethyl sulfoxide;

preferably, the weight to volume ratio of ACP-196 solids to the co-solvent is from 50 mg/1 mL to 200 mg/1 mL;

preferably, the anti-solvent is water;

preferably, the stirring time is from 3 hours to 24 hours;

preferably, the stirring for crystallization and precipitation is carried out at room temperature.

3) Forming a solution of ACP-196 solids in a solvent, stirring for crystallization and precipitation, and then separating and drying to obtain ACP-196 Form 1;

preferably, the solvent is selected from the group consisting of alcohols mixed with water, ketones mixed with water, tetrahydrofuran mixed with water, 1,4-dioxane mixed with water and acetonitrile mixed with water, more preferably ethanol and water mixture;

preferably, the volume percentage of water in the solvent is from 0% to 80%/0, more preferably from 50% to 80%;

preferably, the weight to volume ratio of ACP-196 solids to solvent is from 150 mg/1 mL to 400 mg/1 mL;

preferably, the temperature of forming solution is from 50° C. to 80° C.;

preferably, the crystallization and precipitation temperature is 4° C., and the crystallization and precipitation time is from 2 days to 3 days.

According to the purpose of the invention, the second aspect of the invention is to provide a solid-state ACP-196 Form 2 and its preparation method.

The present invention provides ACP-196 Form 2 with its structure shown in the formula (II) below:

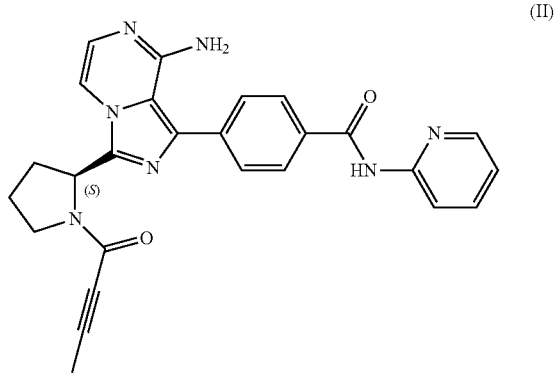

(II)

Using Cu-Kα radiation, the X-ray powder diffraction pattern of ACP-196 Form 2, expressed as 2θ angles, has the following characteristic peaks: 7.4±0.2°, 10.3±0.2°, 12.4±0.2°, 12.7±0.2°, 17.8±0.2° and 21.9±0.2°.

In a preferred embodiment of the present invention, the X-ray powder diffraction pattern of ACP-196 Form 2, expressed as 2θ angles, has the following characteristic peaks: 7.4±0.2°, 8.3±0.2°, 10.3±0.2°, 12.4±0.2°, 12.7±0.2°, 13.9±0.2°, 14.9±0.2°, 17.8±0.2°, 21.9±0.2°, 23.2±0.2°, 24.3±0.2° and 24.9±0.2°.

In a further preferred embodiment of the present invention, the X-ray powder diffraction pattern of ACP-196 Form 2, expressed as 2θ angles, has the following characteristic peaks and relative intensities:

| Diffraction angel 2θ | Relative intensity % |
|---|---|
| 7.4 ± 0.2° | 22.7 |
| 8.3 ± 0.2° | 10.7 |
| 10.3 ± 0.2° | 40.2 |
| 12.4 ± 0.2° | 47.5 |
| 12.7 ± 0.2° | 100.0 |
| 13.1 ± 0.2° | 16.1 |
| 13.9 ± 0.2° | 21.9 |
| 14.5 ± 0.2° | 20.5 |

-continued

| Diffraction angel 2θ | Relative intensity % |
|---|---|
| 14.9 ± 0.2° | 26.5 |
| 17.8 ± 0.2° | 58.5 |
| 21.9 ± 0.2° | 36.8 |
| 23.2 ± 0.2° | 59.1 |
| 24.3 ± 0.2° | 31.6 |
| 24.9 ± 0.2° | 23.1 |
| 25.3 ± 0.2° | 19.3 |

Non-restrictively, in one typical embodiment of the present invention, the X-ray powder diffraction pattern of ACP-196 Form 2 is shown in FIG. 9.

The PLM plot of ACP-196 Form 2 is shown in FIG. 10.

The TGA thermogram of ACP-196 Form 2 is shown in FIG. 11.

Compared with the known amorphous ACP-196, ACP-196 Form 2 has the following beneficial properties:

1) According to the XRPD pattern and PLM plot, ACP-196 Form 2 is a crystalline solid with high crystallinity and good morphology.

2) ACP-196 Form 2 had 0.4% to 0.8% weight loss before 150° C., while amorphous ACP-196 had 11.1% weight loss before 150° C. In amorphous ACP-196 the residual solvents were strongly bonded and at only high temperature the residual solvents can be completely removed. Therefore, ACP-196 Form 2 has less residual solvents.

The above advantageous properties of ACP-196 Form 2 show that, compared with the known amorphous ACP-196, ACP-196 Form 2 has many advantages and is more suitable for being used as the solid form of the active ingredient in pharmaceutical formulations. The amorphous material is unstable and it is prone to crystallize under the influences of environmental factors such as temperature and humidity. Such instability may further affect the quality and stability of the pharmaceutical formulations. ACP-196 Form 2 is crystalline, and its solid form stability is obviously better (than that of amorphous solids). Crystalline solids usually have better flowability and processing (such as filtrating, drying, weighing, screening, etc) characteristics, which are beneficial in improving the homogeneity of active ingredients and pharmaceutical formulations. In addition, ACP-196 Form 2 has lower solvent residue, higher safety, and eliminates subsequent solvent residue removing processes, lowers production costs, improves production efficiency, and also may better ensure the quality of the active ingredients and formulations containing ACP-196 Form 2, avoiding and reducing quality issues, safety issues and stability issues during pharmaceutical production and/or storage, such as content uniformity and impurity issues.

The present invention provides preparation methods of ACP-196 Form 2, which comprise any one of the following preparation methods:

1) Heating ACP-196 Form 1 to a temperature between 120° C. and 130° C., then cooling to room temperature to obtain ACP-196 Form 2;

preferably, the heating rate is from 20° C./min to 50° C./min;

preferably, the cooling rate is from 20° C./min to 40° C./min.

2) Forming a suspension of ACP-196 solids in a solvent, adding seeds of Form 2, stirring for crystallization and precipitation, then separating and drying to obtain ACP-196 Form 2;

preferably, the solvent is selected from the group consisting of alcohols, ketones, esters, tetrahydrofuran, 1,4-dioxane, acetonitrile and toluene, more preferably ethyl acetate;

preferably, the weight to volume ratio of ACP-196 solids to the solvent is from 150 mg/1 mL to 300 mg/1 mL;

preferably, the amount of seeds added is from 10% to 30%;

preferably, the stirring time is from 3 days to 7 days;

preferably, the stirring is carried out at room temperature.

3) Forming a solution of ACP-196 solids in a co-solvent, adding the solution to the anti-solvent containing Form 2 solids, stirring for crystallization and precipitation, and then separating and drying to obtain ACP-196 Form 2;

preferably, the co-solvent is selected from the group consisting of alcohols, ketones, tetrahydrofuran, 1,4-dioxane and acetonitrile, more preferably acetone;

preferably, the weight to volume ratio of ACP-196 solids to the co-solvent is from 100 mg/1 mL to 200 mg/1 mL;

preferably, the anti-solvent is selected from the group consisting of ethers and alkanes, more preferably methyl tert-butyl ether;

preferably, the amount of seeds added is from 10% to 30%;

preferably, the stirring time is from 12 hours to 24 hours;

preferably, the stirring for crystallization and precipitation is carried out at room temperature.

4) Forming a solution of ACP-196 solids in a solvent at 60° C., cooling, adding seeds of Form 2, stirring for crystallization and precipitation, and then separating and drying to obtain ACP-196 Form 2;

preferably, the solvent is a solvent mixture of two solvents selected from the group consisting of alcohols, ketones, esters, ethers and alkanes, more preferably a mixture of isopropyl ether and ethyl acetate;

preferably, the volume ratio of the two solvents in the solvent mixture is 1:1;

preferably, the weight to volume ratio of ACP-196 solids to solvent is from 100 mg/1 mL to 200 mg/1 mL;

preferably, the temperature of forming the solution is from 60° C. to 80° C.;

preferably, the end point of cooling is from 10° C. to 30° C.;

preferably, the amount of seeds added is from 20% to 30%;

preferably, the crystallization and precipitation temperature is room temperature, and the crystallization and precipitation time is from 2 days to 3 days.

According to the purpose of the invention, the third aspect of the invention is to provide a solid-state ACP-196 Form 3 and its preparation method.

Using Cu-Kα radiation, the X-ray powder diffraction pattern of ACP-196 Form 3, expressed as 2θ angles, has the following characteristic peaks: 6.7±0.2°, 9.9±0.2°, 11.0±0.2°, 13.7±0.2°, 14.1±0.2°, 14.4±0.2°, 19.0±0.2°, 20.2±0.2°, 22.6±0.2°, 24.7±0.2°, 26.7±0.2° and 28.3±0.2°.

The present invention provides preparation methods of ACP-196 Form 3, which comprise the following preparation methods: forming a suspension of ACP-196 in mixed solvents containing water, stirring at low temperature for crystallization and precipitation, then separating to obtain ACP-196 Form 3;

Preferably, the mixed solvent containing water is a mixture of water and acetone, the volume percentage of the water is 85%, the weight-volume ratio of ACP-196 solids to solvent is 100 mg/1 mL, and the stirring time is 3 days.

Non-restrictively, in one typical embodiment of the present invention, the X-ray powder diffraction pattern of ACP-196 Form 3 is shown in FIG. 12.

According to the purpose of the invention, the fourth aspect of the invention is to provide ACP-196 Form 4. Non-restrictively, in one typical embodiment of the present invention, the X-ray powder diffraction pattern of ACP-196 Form 4 is shown in FIG. 13.

In the preparation methods of ACP-196 forms of the invention, the starting material "ACP-196 solids" may be a disclosed ACP-196 compound including an amorphous ACP-196, for example, but not limited to, ACP-196 prepared according to any one of the preparation methods in patent document CN103889987A. These patent documents are incorporated herein by reference in their entirety.

The terms used in the present invention include:

The "room temperature" is a temperature between 10° C. and 30° C.

"Stirring" may be carried out by a conventional stirring method in the art, such as magnetic stirring, mechanical stirring, and the stirring speed is 50 to 1800 r/min, preferably 300 to 900 r/min.

"Separating" may be performed using conventional methods in the field, such as centrifugation or filtration. Preferred method is vacuum filtration, generally at a pressure less than atmospheric pressure at room temperature, preferably less than 0.09 MPa.

"Drying" may be performed by routine methods in the field, such as room temperature drying, forced air drying or vacuum drying. Drying is performed under reduced pressure or atmospheric pressure, and pressure less than 0.09 MPa is preferred. Drying instruments and methods are unrestricted, and may be fume hood, blast oven, spray drying, fluidized bed drying or vacuum oven.

The term "co-solvent" refers to a solvent with good solubility for a compound.

The term "anti-solvent" refers to a solvent insoluble or essentially insoluble to a compound.

In the present invention, "crystal" or "crystalline form" refers to that characterized by X-ray powder diffraction pattern, having a unique ordered molecular arrangement or configuration within the crystalline lattice. It is known to those skilled in the field that the experimental error depends on instrumental conditions, sample preparation and sample purity. The 2θ angle of the peaks in the XRPD pattern may change with the change of instrument and samples. The difference of peak position may vary by 1°, 0.8°, 0.5°, 0.3°, 0.1°, etc., depending on the instruments and samples, and ±0.2° in error is usually allowed. Therefore the difference in peak position should not be regarded as the only factor. The relative intensity of peaks may change with the change of sample, sample preparation, and other experimental conditions. Therefore, the order of peak intensities should not be regarded as the only or the determining factor. Due to the effect of experimental factors including sample height, peak position may shift. Generally, a small amount of peak shifting is acceptable. Hence, it is easily understood for those skilled in the field that any crystalline form having the same or similar x-ray powder diffraction pattern as that of the crystalline form in the present invention should be within the scope of the present invention. "Single crystalline form" refers to a crystalline form confirmed by x-ray powder diffraction as a single form.

ACP-196 forms of the present invention are substantially pure, single, or substantially free of any other crystalline or amorphous forms. As used herein, "substantially pure" when used in reference to a new crystalline form means that the new crystalline form comprises at least 80% by weight of the present compound, more preferably at least 90% (by weight), especially at least 95% (by weight), especially at least 99% (by weight).

The fifth aspect of the invention is to provide a pharmaceutical composition, which comprises a therapeutically and/or preventively effective amount of pharmaceutical active ingredient selected from the crystalline forms of ACP-196 of the present invention or the crystalline forms of ACP-196 prepared by the preparation methods of the present invention, and at least one pharmaceutically acceptable excipient or carrier. Wherein ACP-196 forms of the present invention include Form 1 and Form 2. In addition, the pharmaceutical composition may also comprise other pharmaceutically acceptable salts, crystalline forms or amorphous forms of ACP-196. The dosage form of the compound used in the method of the present invention may be determined by selecting specific solid state of the compound, the type of pharmacokinetic distribution required by the route of administration and the status of the patient.

The compound of the present invention may be formulated for oral, sublingual, subcutaneous, intravenous, intramuscular, nasal, topical or rectal administration according to generally accepted methods in the pharmaceutical field, and the formulations contain at least one active compound, preferably in the form of a unit dosage form for administration. The human dose preferably contains 0.001 to 25 mg/kg body weight.

The pharmaceutical composition may be prepared as a certain dosage form depending on the route of administration or need, and may be solid or liquid. Solid oral dosage forms, include, for example, tablets, granules, powders, pills, and capsules; liquid oral dosage forms, include, for example, solutions, syrups, suspensions, dispersions, and emulsions; injectables includes, for example, solutions, dispersions and lyophilized products. The formulation may be suitable for immediate, sustained or controlled release of the active ingredient of the drug. It may be a conventional, dispersible, chewable, buccal soluble or rapidly dissolvable formulation.

The excipients of pharmaceutical composition are known to those skilled in the field, and the selection of the type, usage and amount of the excipients is also known to those skilled in the field. For example, they include carbohydrate, cellulose and its derivative, starch or modified starch, solid inorganics such as calcium phosphate, dicalcium phosphate, hydroxyapatite, calcium sulfate, calcium carbonate, semi-solid such as lipids or paraffin wax, adhesives such as microcrystalline cellulose, ethyl cellulose, hydroxymethyl cellulose, hydroxypropyl methyl cellulose, hydroxyethyl cellulose, glidants such as colloidal silica dioxide, light anhydrous silicic acid, crystalline cellulose, talcum powder or magnesium stearate, disintegrants such as sodium glycolate starch, crospovidone, croscarmellose, sodium carboxymethylcellulose, cornstarch, lubricant such as stearic acid, magnesium stearate, sodium stearyl fumarate, polyethyleneglycol.

For making solid dosage units, the use of conventional additives such as filters, colorants, adhesives and the like is expected. In general any inactive pharmaceutically acceptable carriers can be used. the active ingredient of the present invention can be administered together with these carriers as solid compositions. Suitable carriers include lactose, starch, sucrose, glucose, methyl cellulose, or mixtures thereof, and can be used in suitable amount. For parenteral administration, aqueous suspensions, isotonic saline solutions and sterile injectable solutions containing pharmaceutically acceptable dispersing agents and/or wetting agents, such as propylene glycol or butylene glycol can be used.

The pharmaceutical composition may be prepared by the method commonly known to those skilled in the art. In preparation of the pharmaceutical composition, the ACP-196 form of the present invention (including ACP-196 Form 1 and ACP-196 Form 2) is mixed with one or more pharmaceutically acceptable excipients, optionally with other pharmaceutically acceptable polymorphs, salt forms and amorphous form of ACP-196, optionally with one or more other active ingredients. Solid formulations may be prepared by direct mixing, granulation and other processes.

For oral administration, the active ingredient may be presented as discrete units, such as tablets, capsules, powders, granulates, solutions, suspensions, etc.

For parenteral administration, the pharmaceutical composition of the present invention may be presented in unit-dose or multidose containers, e.g. injection liquids in predetermined amounts, for example in sealed vials and ampoules, and may be stored in a freeze dried (lyophilized) condition.

According to the purpose of the present invention, the present invention provides ACP-196 or crystalline forms of ACP-196 or crystalline forms of ACP-196 prepared by the preparation methods of the present invention for the preparation of drugs for the treatment or prevention of tyrosine kinases such as Bruton tyrosine kinase (BTK) mediated diseases or conditions. The crystalline forms of ACP-196 of the present invention include ACP-196 Form 1 and ACP-196 Form 2. The disease or condition mediated by BTK refers to any disease or other harmful condition in which B cells, mast cells, myeloid cells or osteoclasts play a center role. These diseases include, but are not limited to, immune, autoimmune and inflammatory diseases, allergies, infectious diseases, bone resorption diseases and proliferative diseases. The immune, autoimmune and inflammatory diseases described include, but are not limited to, such as rheumatic diseases (such as arthritis, rheumatoid arthritis, psoriatic arthritis, osteoarthritis, infective arthritis, progressive chronic arthritis, teratogenic arthritis, osteoarthritis, juvenile arthritis, traumatic arthritis, gouty arthritis, Reiter's syndrome, polychondritis, acute synovitis and spondylitis etc.), glomerulonephritis (with or without nephrotic syndrome), autoimmune hematological disorders (such as hemolytic anemia, aplastic anemia, idiopathic thrombocytopenia and neutropenia), autoimmune gastritis and autoimmune inflammatory bowel diseases (such as ulcerative colitis and Crohn's disease), graft-versus-host disease, homology allograft rejection, chronic thyroiditis, Graves' disease, scleroderma, diabetes (type I and II), active hepatitis (acute and chronic), autoimmune hepatitis, pancreatitis, primary biliary cirrhosis, endometriosis, myasthenia gravis, multiple sclerosis, lupus, psoriasis, atopic dermatitis, contact dermatitis, eczema, skin sunburn, vasculitis (e.g. Behcet's disease), chronic renal insufficiency, Stevens-Johnson syndrome, inflammatory pain, idiopathic sprue, cachexia, sarcoidosis, infectious neuropathy (Guillain-Barré syndrome), uveitis, conjunctivitis, keratoconjunctivitis, otitis media, periodontitis, pulmonary interstitial fibrosis, asthma, appendix inflammation, bronchiolitis, bronchitis, rhinitis, sinusitis, pneumoconiosis, pulmonary insufficiency syndrome, emphysema, pulmonary fibrosis, silicosis, chronic inflammatory pulmonary disease (such as chronic obstructive pulmonary disease) and other inflammatory or obstructive diseases of the respiratory tract.

Allergies that can be treated or prevented include, for example, food, food additives, insect toxins, dust mites, pollen, animal materials and contact allergens, type I hypersensitivity, allergic asthma, allergic rhinitis, allergies conjunctivitis or atopic dermatitis.

Infectious diseases that can be treated or prevented include, but are not limited to, for example, sepsis, septic shock, endotoxic shock, sepsis caused by gram-negative bacteria, *shigella*, meningitis, pleurisy, cerebral malaria, pneumonia, tuberculosis, endocarditis, viral myocarditis, viral hepatitis (hepatitis A, hepatitis B and hepatitis C), nephritis, HIV infection, tendinitis, retinitis, influenza, herpes, infections associated with severe burns, myalgia caused by infection, cachexia secondary to infection, and infection caused by animal viruses.

Bone resorption diseases and conditions that can be treated or prevented include, for example, osteoporosis, osteoarthritis, traumatic arthritis, gouty arthritis, and bone disorders associated with multiple myeloma.

Proliferative diseases that can be treated or prevented include, for example, B cell proliferative diseases such as diffuse large B cell lymphoma, mantle cell lymphoma (MCL), follicular lymphoma, chronic lymphocytic lymphoma, chronic lymphocytic leukemia, B cell pro-lymphocytic leukemia, acute lymphocytic leukemia (ALL), lymphoplasmacytic lymphoma/macroglobulinemia, spleen marginal lymphoma, plasma cell myeloma, plasmacytoma, extranodal marginal zone B cell lymphoma, lymph node marginal zone B cell lymphoma, mantle cell lymphoma, mediastinal (thymus) large B cell lymphoma, intravascular large B cell lymphoma, primary exudative lymphoma, Burkittlymphoma/leukemia or lymphomatoid granulomatosis. The crystalline forms of the compounds of the invention are especially useful for the treatment of B cell lymphomas caused by chronic active B cell receptor signaling.

A method of treating and/or preventing a Bruton's tyrosine kinase (BTK) mediated disease, according to the object of the invention, comprising administering to a patient in need thereof a prophylactically, inhibitory and/or therapeutically effective amount of one or more of ACP-196 Form 1 or ACP-196 Form 2 of the present invention, or a pharmaceutical composition containing one or more of ACP-196 Form 1 or ACP-196 Form 2 of the present invention; the disease is described in the specification section of the present invention. The effective amount, for example, a human dose for parenteral administration, preferably contains from 0.001 to 25 mg/kg body weight. The desired dose can be presented as a single dose or as multiple sub-doses administered at appropriate intervals throughout the day, or in the case of a female recipient, at a suitable daily interval during the menstrual cycle. The dosage and dosage regimen can vary between female and male recipients.

SPECIFIC IMPLEMENTATIONS

The following examples will help to further understand the present invention, but are not intended to limit the contents of the present invention.

Instruments and characterization methods:

X-ray powder diffraction (XRPD): performed on Bruder D8 Advance diffractometer. Samples were tested at room temperature. Testing conditions: 2θ scan range 3-40°, step size 0.02°, and speed 0.2 s/step.

Polarized light microscopy (PLM) plots were collected on XP~500E polarized light microscopy. Took a small amount of powder sample on a glass and added some mineral oil. Covered with the cover glass, placed it on the stage for observation and took a picture.

Differential thermal analysis data were collected on TA Instruments Q200 DSC. Method: A sample of 1 to 10 mg was placed in a sealed aluminum pan, and the sample was heated from room temperature to 200° C. at a heating rate of 10° C./min under the protection of dry nitrogen purge at 40 mL/min.

Thermogravimetric analysis data were collected on TA Instruments Q500 TGA. Method: A sample of 5 to 15 mg was placed in a platinum pan, using High Resolution™, the sample was heated from room temperature to 350° C. at a heating rate of 10° C./min under the protection of dry nitrogen purge at 40 mL/min.

Dynamic vapor sorption data and isothermal sorption data were collected on TA Instruments Q5000 TGA. Method: A sample of 1 to 10 mg was placed in a platinum pan; the weight change of the sample during the change in relative humidity from 0% to 80% to 0% was measured.

Unless particularly specified, all reagents used in the embodiments were commercially available.

Unless particularly specified, all embodiments were operated at room temperature.

Preparation Example 1 Prepare ACP-196

The ACP-196 prepared by referencing the methods described in Example 6 of patent document CN103889987A. Data: LCMS(B)Rt: 2.08 min: m/z 466.1 (M+H)+.

Figure 1:
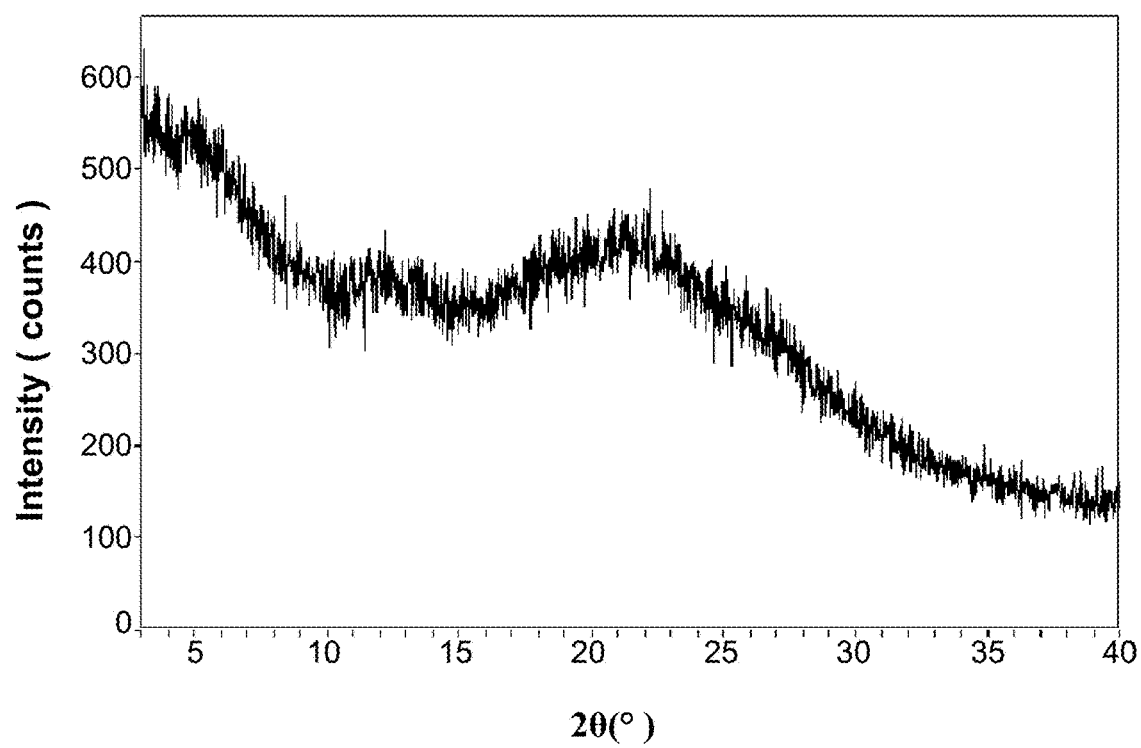
FIG. 1 is the XRPD pattern of amorphous ACP-196 prepared according to CN103889987A.
Figure 2:
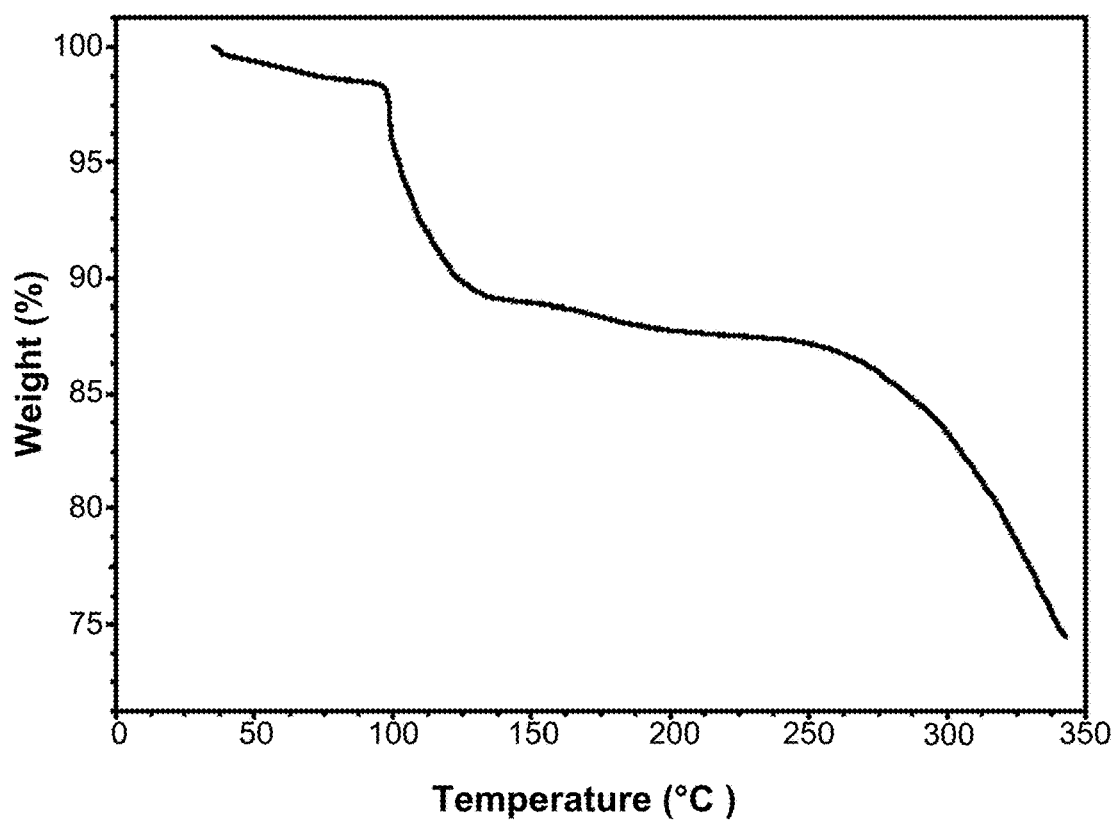
FIG. 2 is the TGA thermogram of amorphous ACP-196 prepared according to CN103889987A.
Figure 3:
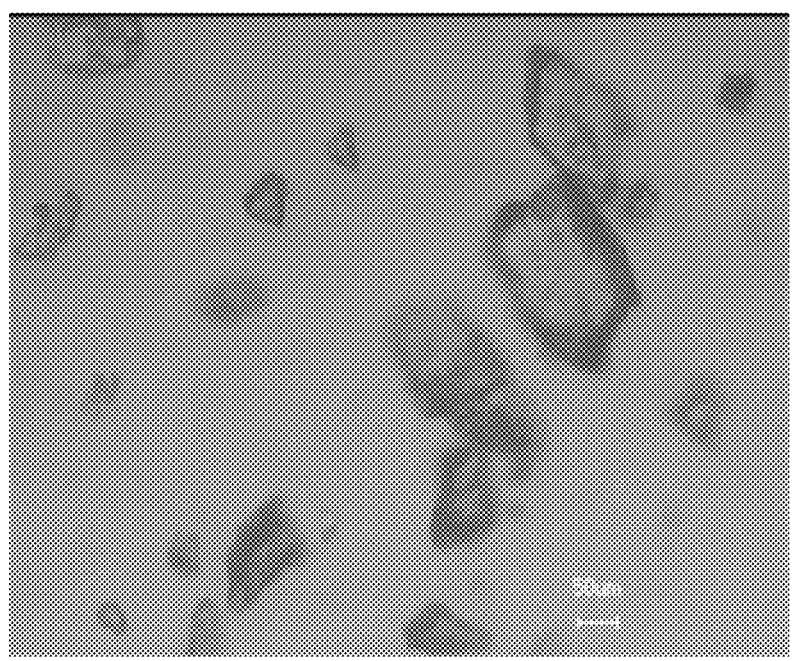
FIG. 3 is the PLM plot of amorphous ACP-196 prepared according to CN103889987A.
Figure 4:
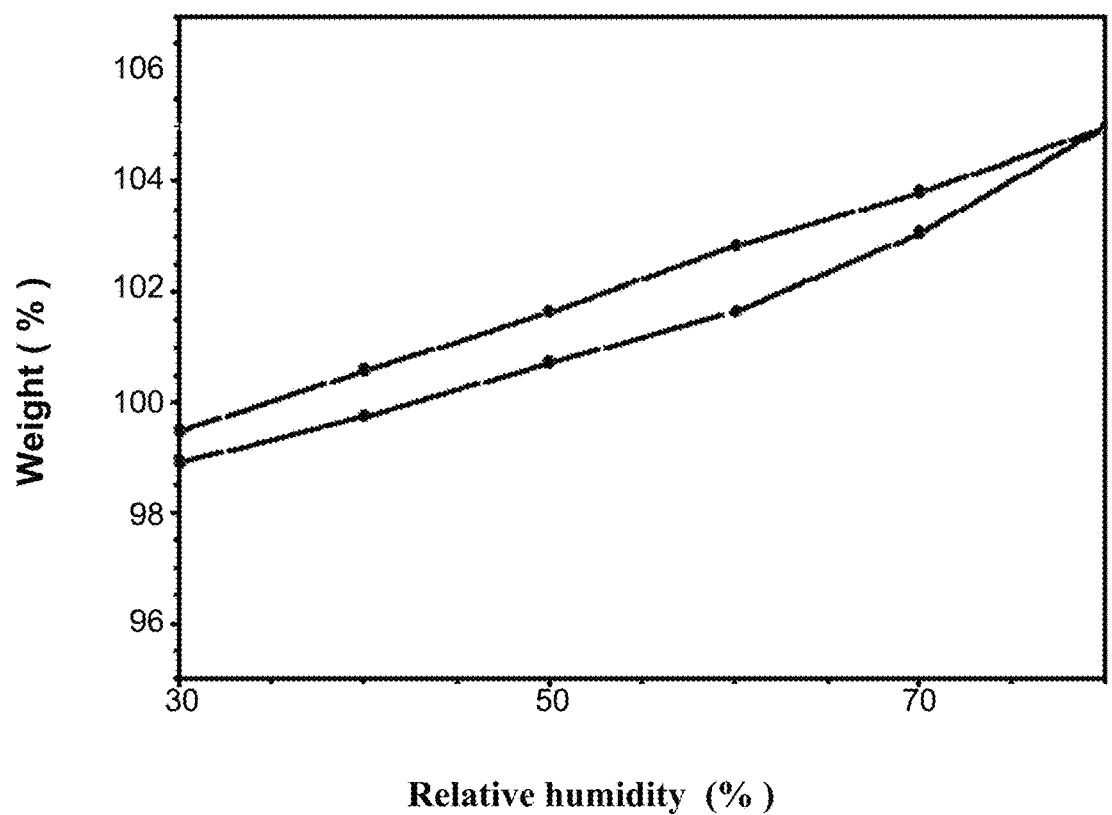
FIG. 4 is the isothermal sorption plot of amorphous ACP-196 prepared according to CN103889987A.

Its XRPD pattern is shown in FIG. 1.
Its TGA thermogram is shown in FIG. 2.
Its PLM plot is shown in FIG. 3.
Its isothermal sorption plot is shown in FIG. 4.

The above characterization results indicate that ACP-196 obtained by the method described in Example 6 of patent document CN100352817A is an amorphous substance.

Example 1

Took 500 mg ACP-196 of Preparation Example 1, added water-acetonitrile solution (containing 75% water) 20 mL to obtain a suspension, stirred at 40° C. for crystallization and precipitation for 7 days, filtrated, and then vacuum dried at room temperature overnight to obtain 400 mg ACP-196 Form 1; 74% yield.

Figure 5:
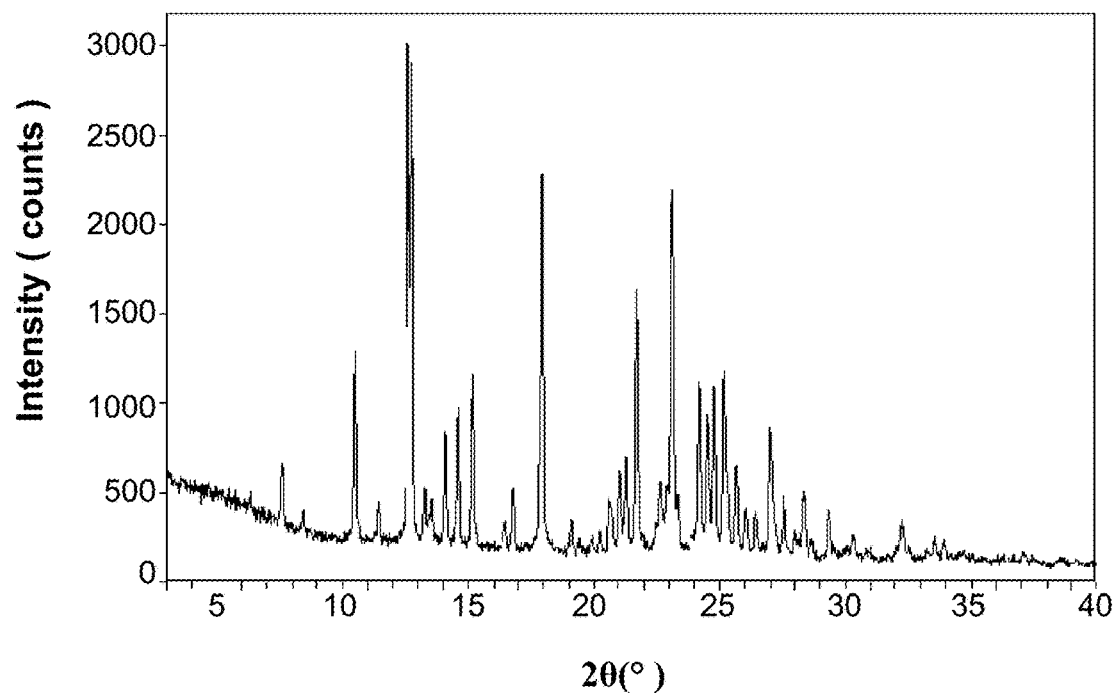
FIG. 5 is the XRPD pattern of ACP-196 Form 1 prepared according to Example 1 of the present invention.
Figure 6:
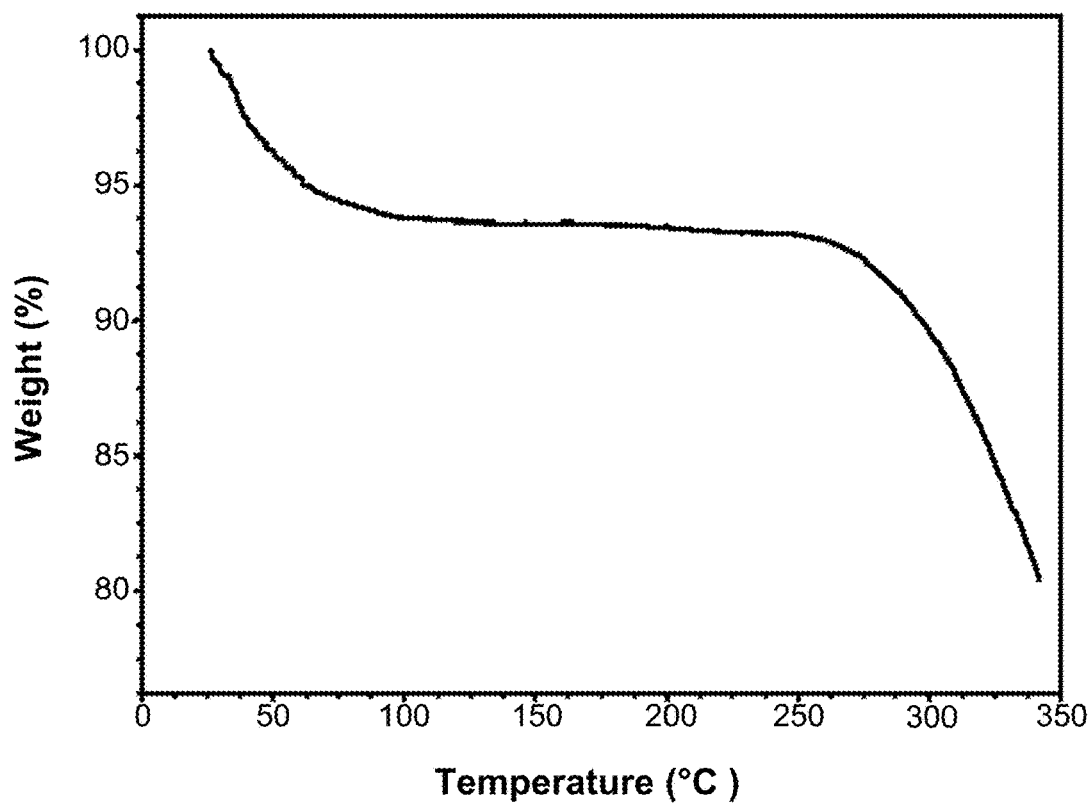
FIG. 6 is the TGA thermogram of ACP-196 Form 1 prepared according to Example 1 of the present invention.
Figure 7:
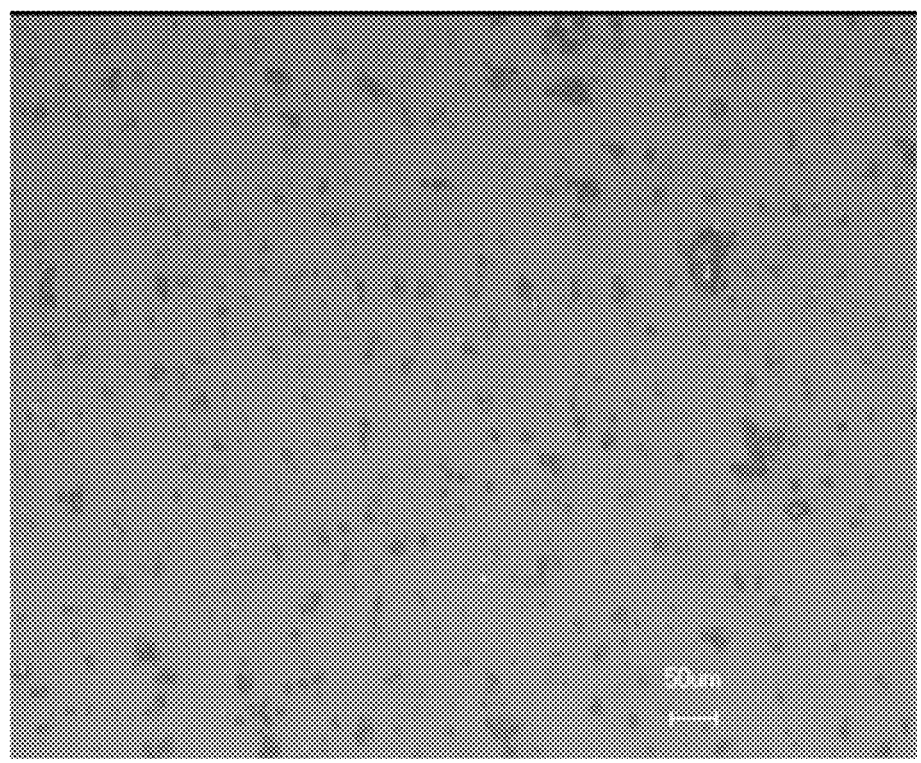
FIG. 7 is the PLM plot of ACP-196 Form 1 prepared according to Example 1 of the present invention.
Figure 8:
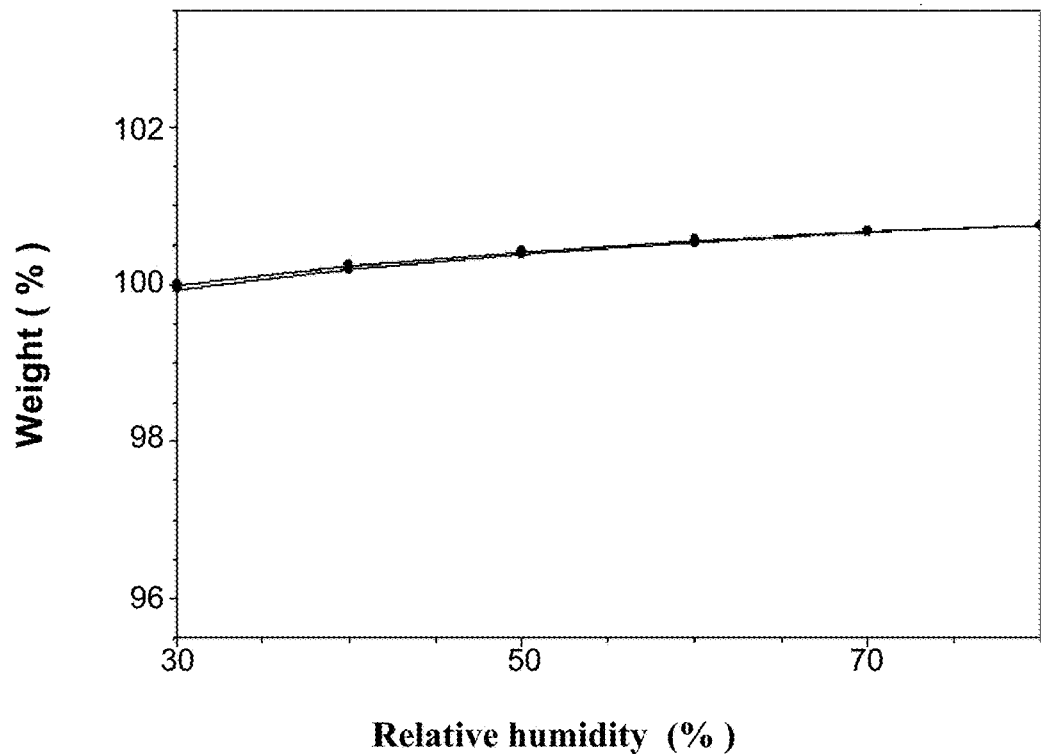
FIG. 8 is the isothermal sorption plot of ACP-196 Form 1 prepared according to Example 1 of the present invention.

Its XRPD pattern is shown in FIG. 5.
Its TGA thermogram is shown in FIG. 6.
Its PLM plot is shown in FIG. 7.
Its isothermal sorption plot is shown in FIG. 8.

Example 2

Took 100 mg ACP-196 of Preparation Example 1, added water-acetonitrile solution (containing 80% water) 1 mL to obtain a suspension, stirred at 25° C. for crystallization and precipitation for 7 days, filtrated, and then vacuum dried at room temperature overnight to obtain 90 mg ACP-196 Form 1; 84% yield.

Example 3

Took 200 mg ACP-196 of Preparation Example 1, added water-acetonitrile solution (containing 50% water) 4 mL to obtain a suspension, stirred at 30° C. for crystallization and precipitation for 3 days, filtrated, and then vacuum dried at room temperature overnight to obtain 175 mg ACP-196 Form 1; 81% yield.

Example 4

Took 20 mg ACP-196 of Preparation Example 1, added 0.8 mL water to obtain a suspension, stirred at 40° C. for crystallization and precipitation for 5 days, filtrated, and then vacuum dried at room temperature overnight to obtain 10 mg ACP-196 Form 1; 46% yield.

Example 5

Took 50 mg ACP-196 of Preparation Example 1, added water-acetonitrile solution (containing 70% water) 1 mL to obtain a suspension, stirred at 40° C. for crystallization and precipitation for 7 days, filtrated, and then vacuum dried at room temperature overnight to obtain 30 mg ACP-196 Form 1; 56% yield.

Example 6

ACP-196 Form 1 can also be obtained by replacing the solvents in Example 5 with the following table.

| Experiment Number | Solvent 1 | Solvent 2 |
|---|---|---|
| Experiment 1 | water | Methanol |
| Experiment 2 | water | Ethanol |
| Experiment 3 | water | Isopropanol |
| Experiment 4 | water | n-Propanol |
| Experiment 5 | water | sec-Butanol |
| Experiment 6 | water | n-Butanol |
| Experiment 7 | water | Acetone |
| Experiment 8 | water | Butanone |
| Experiment 9 | water | Tetrahydrofuran |
| Experiment 10 | water | 1,4-dioxane |

Example 7

Placed 200 mg ACP-196 of Preparation Example 1 in 1 mL dimethyl sulfoxide to obtain a clear solution, added 2 mL water, precipitated crystals, stirred for crystallization and precipitation at room temperature for 3 hours, filtrated, and then vacuum dried at room temperature overnight to obtain 150 mg ACP-196 Form 1; 70% yield.

Example 8

Placed 50 mg ACP-196 of Preparation Example 1 in 1 mL ethanol to obtain a clear solution, added 4 mL water, precipitated crystals, stirred at room temperature for crystallization and precipitation for 24 hours, filtrated, and then vacuum dried at room temperature overnight to obtain 35 mg ACP-196 Form 1; 65% yield.

Example 9

ACP-196 Form 1 can also be obtained by replacing the solvents in Example 8 with the following table.

| Experiment Number | Co-solvent | Anti-solvent |
| --- | --- | --- |
| Experiment 1 | Methanol | Water |
| Experiment 2 | Trifluoroethanol | Water |
| Experiment 3 | Isopropanol | Water |
| Experiment 4 | n-Propanol | Water |
| Experiment 5 | Acetone | Water |
| Experiment 6 | Tetrahydrofuran | Water |
| Experiment 7 | 1,4-dioxane | Water |
| Experiment 8 | Acetonitrile | Water |

Example 10

Took 200 mg ACP-196 of Preparation Example 1, added 0.5 mL ethanol at 60° C. to obtain a clear solution, stirred at 4° C. for crystallization and precipitation for 2 days, filtrated, and then vacuum dried at room temperature overnight to obtain 120 mg ACP-196 Form 1; 56% yield.

Example 11

Took 150 mg ACP-196 of Preparation Example 1, added water-ethanol solution (containing 80% water) 1 mL at 60° C. to obtain a clear solution, stirred at 4° C. for crystallization and precipitation for 3 days, filtrated, and then vacuum dried at room temperature overnight to obtain 86 mg ACP-196 Form 1; 53% yield.

Example 12

Took 150 mg ACP-196 of Preparation Example 1, added water-ethanol solution (containing 50% water) 0.5 mL containing 50% water to obtain a clear solution, stirred at 4° C. for crystallization and precipitation for 3 days, filtrated, and then vacuum dried at room temperature overnight to obtain 103 mg ACP-196 Form 1; 64% yield.

Example 13

ACP-196 Form 1 can also be obtained by replacing the solvents in Example 12 with the following table.

| Experiment Number | Temperature (° C.) | Solvent 1 | Solvent 2 |
| --- | --- | --- | --- |
| Experiment 1 | 50 | Methanol | Water |
| Experiment 2 | 60 | Trifluoroethanol | Water |
| Experiment 3 | 60 | Isopropanol | Water |
| Experiment 4 | 60 | n-Propanol | Water |
| Experiment 5 | 50 | Acetone | Water |
| Experiment 6 | 50 | Tetrahydrofuran | Water |
| Experiment 7 | 80 | 1,4-dioxane | Water |
| Experiment 8 | 70 | Acetonitrile | Water |

XRPD patterns, PLM plots, TGA thermograms, isothermal sorption plots (not shown) of the samples prepared in Examples 2 to 13 are the same as or similar to that of the sample prepared in Example 1, indicating the crystalline forms obtained in Examples 2 to 13 are the same as that of Example 1.

Example 14

Took 200 mg ACP-196 Form 1 of the present invention, heated to 120° C. at the rate of 20° C./min, kept for 5 min, and then cooled to room temperature at the rate of 20° C./min to obtain 286 mg ACP-196 Form 2; 93% yield.

Figure 9:
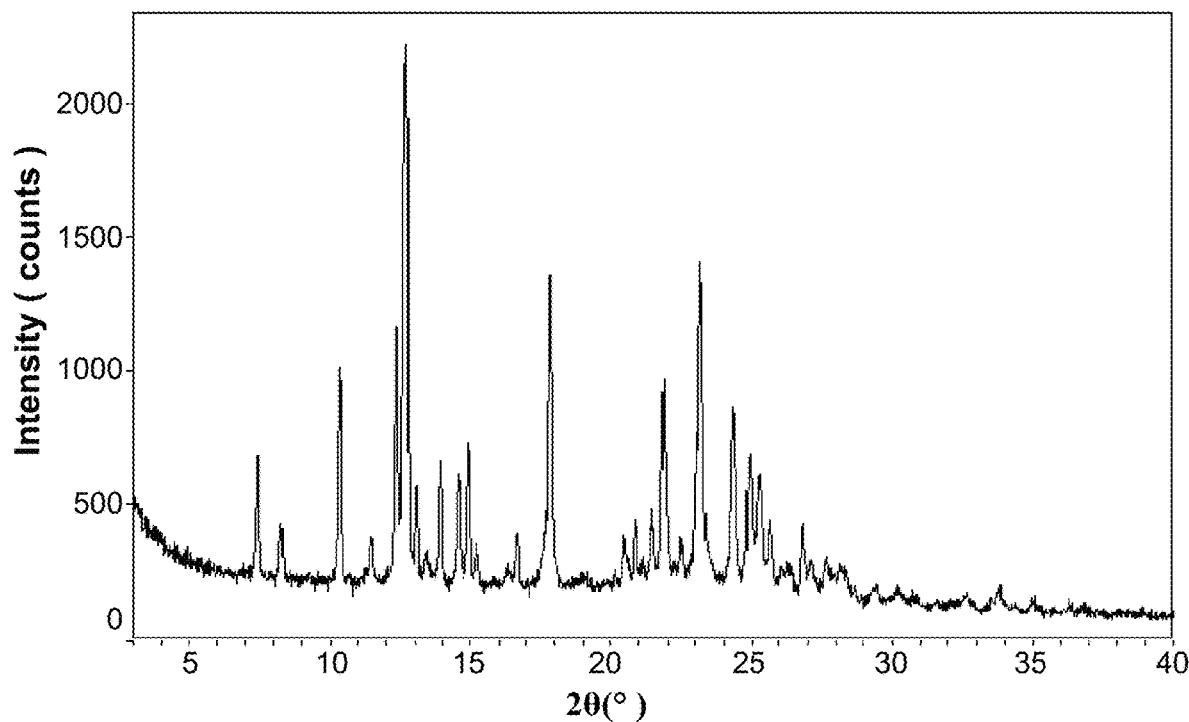
FIG. 9 is the XRPD pattern of ACP-196 Form 2 prepared according to Example 7 of the present invention.
Figure 10:
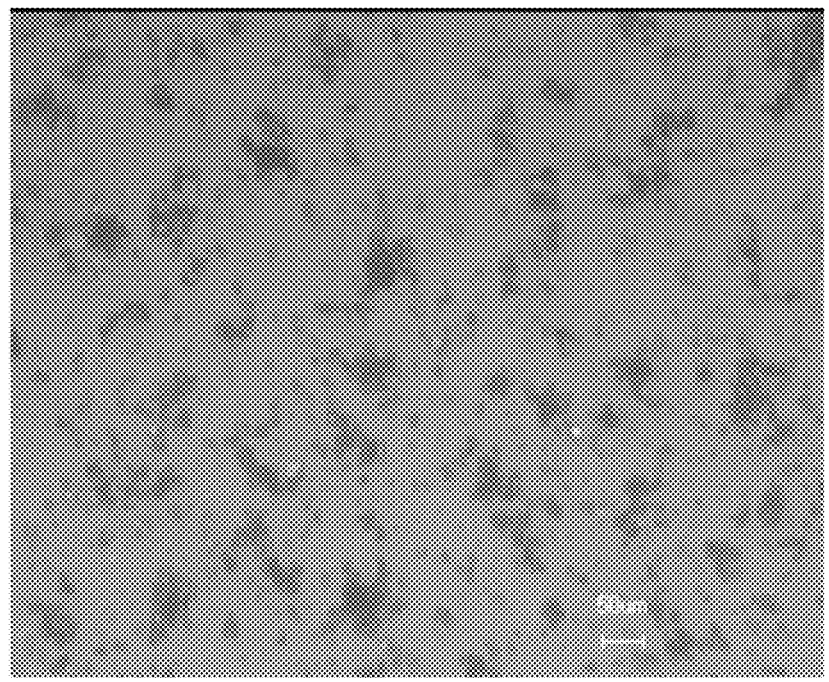
FIG. 10 is the PLM plot of ACP-196 Form 2 prepared according to Example 7 of the present invention.
Figure 11:
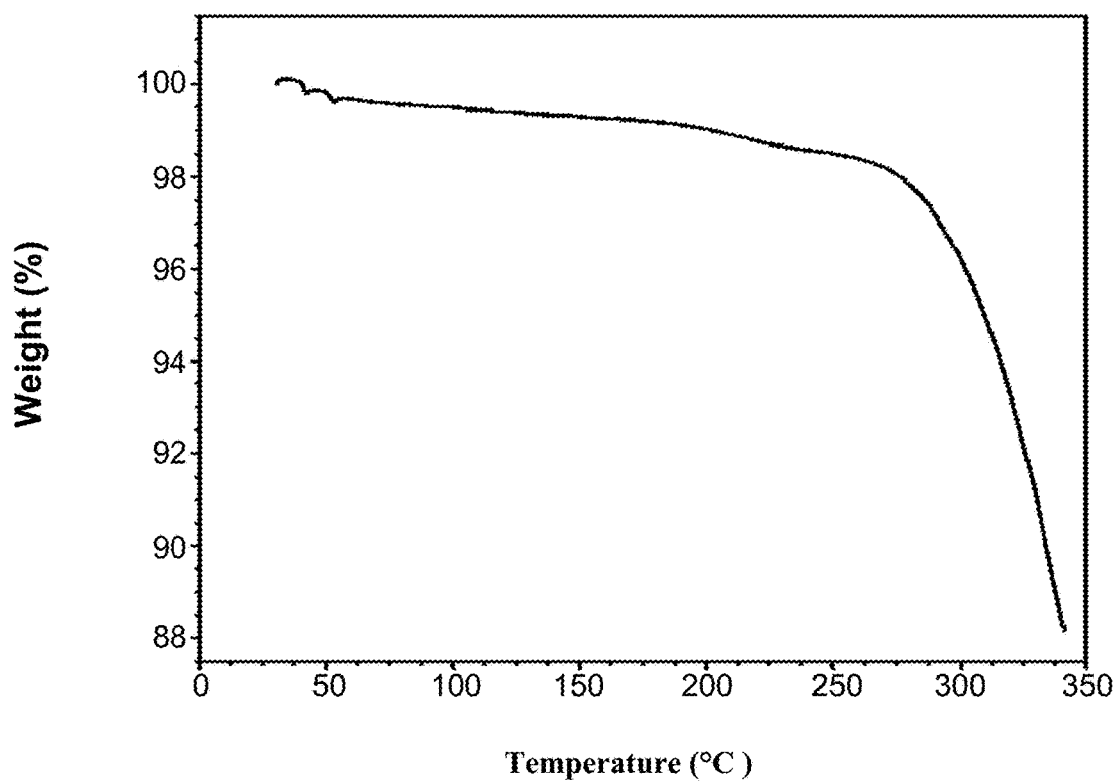
FIG. 11 is the TGA thermogram of ACP-196 Form 2 prepared according to Example 7 of the present invention.

Its XRPD pattern is shown in FIG. 9.
Its PLM plot is shown in FIG. 10.
Its TGA thermogram is shown in FIG. 11.

Example 15

Took 150 mg ACP-196 of Preparation Example 1, added 1 mL ethyl acetate to obtain a suspension, added 45 mg ACP-196 Form 2 prepared in Example 14, stirred at room temperature for crystallization and precipitation for 3 days, filtrated, and then vacuum dried at room temperature overnight to obtain 119 mg ACP-196 Form 2; 61% yield.

Example 16

Took 300 mg ACP-196 of Preparation Example 1, added 1 mL ethyl acetate to obtain a suspension, added 30 mg ACP-196 Form 2 prepared in Example 14, stirred at room temperature for crystallization and precipitation for 7 days, filtrated, and then vacuum dried at room temperature overnight to obtain 232 mg ACP-196 Form 2; 70% yield.

Example 17

ACP-196 Form 2 can also be obtained by replacing the solvents in Example 16 with the following table.

| Experiment Number | Solvent |
| --- | --- |
| Experiment 1 | Ethanol |
| Experiment 2 | Isopropanol |
| Experiment 3 | sec-Butanol |
| Experiment 4 | Acetone |
| Experiment 5 | Isopropyl acetate |
| Experiment 6 | Tetrahydrofuran |
| Experiment 7 | 1,4-dioxane |
| Experiment 8 | Acetonitrile |
| Experiment 9 | Toluene |

Example 18

Placed 200 mg ACP-196 of Preparation Example 1 in 1 mL acetone to obtain a clear solution, added the solution dropwise to methyl tert-butyl ether containing 20 mg ACP- 196 Form 2 prepared in Example 17, stirred at room temperature for crystallization and precipitation for 12 hours, filtrated and then vacuum dried at room temperature overnight to obtain 173 mg ACP-196 Form 2; 79% yield.

Example 19

Placed 200 mg ACP-196 of Preparation Example 1 in 2 mL acetone to obtain a clear solution, added the solution dropwise to methyl tert-butyl ether containing 60 mg ACP-196 Form 2 prepared in Example 17, stirred at room temperature for crystallization and precipitation for 12 hours, filtrated and then vacuum dried at room temperature overnight to obtain 173 mg ACP-196 Form 2; 66% yield.

Example 20

ACP-196 Form 2 can also be obtained by replacing the solvents in Example 19 with the following table.

| Experiment Number | Co-solvent | Anti-solvent |
|---|---|---|
| Experiment 1 | Ethanol | Heptane |
| Experiment 2 | Isopropyl | Isopropyl ether |
| Experiment 3 | Butanone | Methylcyclohexane |
| Experiment 4 | Tetrahydrofuran | Heptane |
| Experiment 5 | 1,4-dioxane | Isopropyl ether |
| Experiment 6 | Acetonitrile | Methyl tert-butyl ether |

Example 21

Took 150 mg ACP-196 of Preparation Example 1, added 1.5 mL isopropyl ether/ethyl acetate mixture (1:1 volume ratio) at 60° C. to obtain a clear solution, cooled to 35° C. and added 30 mg ACP-196 Form 2 prepared in Example 17, kept for 1 hour, then stirred at room temperature for crystallization and precipitation for 2 days, filtrated, and then vacuum dried at room temperature overnight to obtain 101 mg ACP-196 Form 2; 56% yield.

Example 22

Took 200 mg ACP-196 of Preparation Example 1, added 1 mL isopropyl ether/ethyl acetate (volume ratio 1:1) at 60° C. to obtain a clear solution, cooled to 40° C. and added 60 mg ACP-196 Form 2 prepared in Example 17, kept for 1 hour, then stirred at room temperature for crystallization and precipitation for 3 days, filtrated, and then vacuum dried at room temperature overnight to obtain 101 mg ACP-196 Form 2; 56% yield.

Example 23

Form 2 can also be obtained by replacing the solvents in Example 22 with the following table.

| Experiment Number | Temperature (° C.) | Solvent 1 | Solvent 2 |
|---|---|---|---|
| Experiment 1 | 80 | Ethanol | Heptane |
| Experiment 2 | 60 | Acetone | Methyl tert-butyl ether |
| Experiment 3 | 70 | Isopropyl acetate | Methylcyclohexane |
| Experiment 4 | 60 | Isopropyl acetate | Isopropyl ether |

Example 24

Took 30 mg ACP-196 Form 1 of the present invention, heated to 125° C. at the rate of 50° C./min, kept for 5 min, and then cooled to room temperature at the rate of 30° C./min to obtain 26 mg ACP-196 Form 2; 87% yield.

Example 25

Took 40 mg ACP-196 Form 1 of the present invention, heated to 130° C. at the rate of 30° C./min, kept for 5 min, and then cooled to room temperature at the rate of 40° C./min to obtain 36 mg ACP-196 Form 2; 90% yield.

XRPD patterns, PLM plots, TGA thermograms (not shown) of the samples prepared in Examples 15 to 25 are the same as or similar to that of the sample prepared in Example 14, indicating the crystalline forms obtained in Examples 15 to 25 are the same as that of Example 14.

Example 26

Took 100 mg ACP-196 of Preparation Example 1, added water-acetone solution containing 85% water 1 mL to obtain a suspension, stirred at 5° C. for crystallization and precipitation for 7 days, and then filtrated to obtain ACP-196 Form 3.

Figure 12:
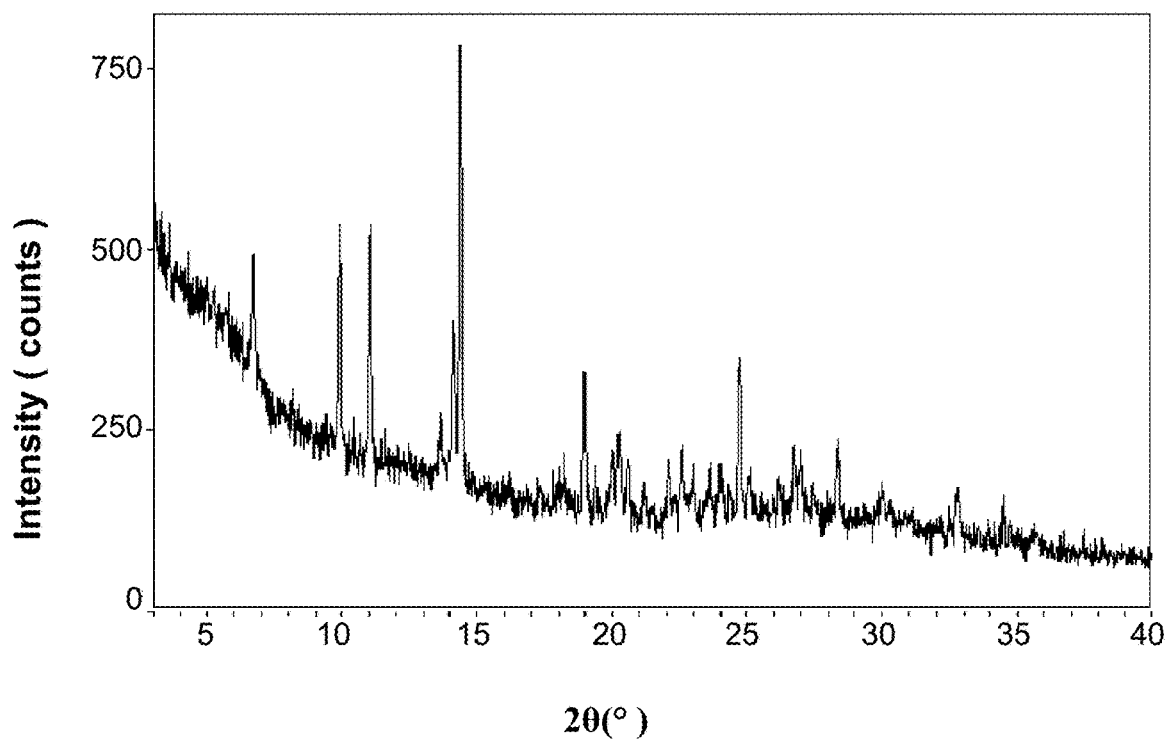
FIG. 12 is the XRPD pattern of ACP-196 Form 3 prepared according to Example 11 of the present invention.

Its XRPD pattern is shown in FIG. 12.

Example 27

Took a proper amount of ACP-196 Form 1 of Example 1, heated to 130° C. at a rate of 20° C./min to obtain ACP-196 Form 4.

Figure 13:
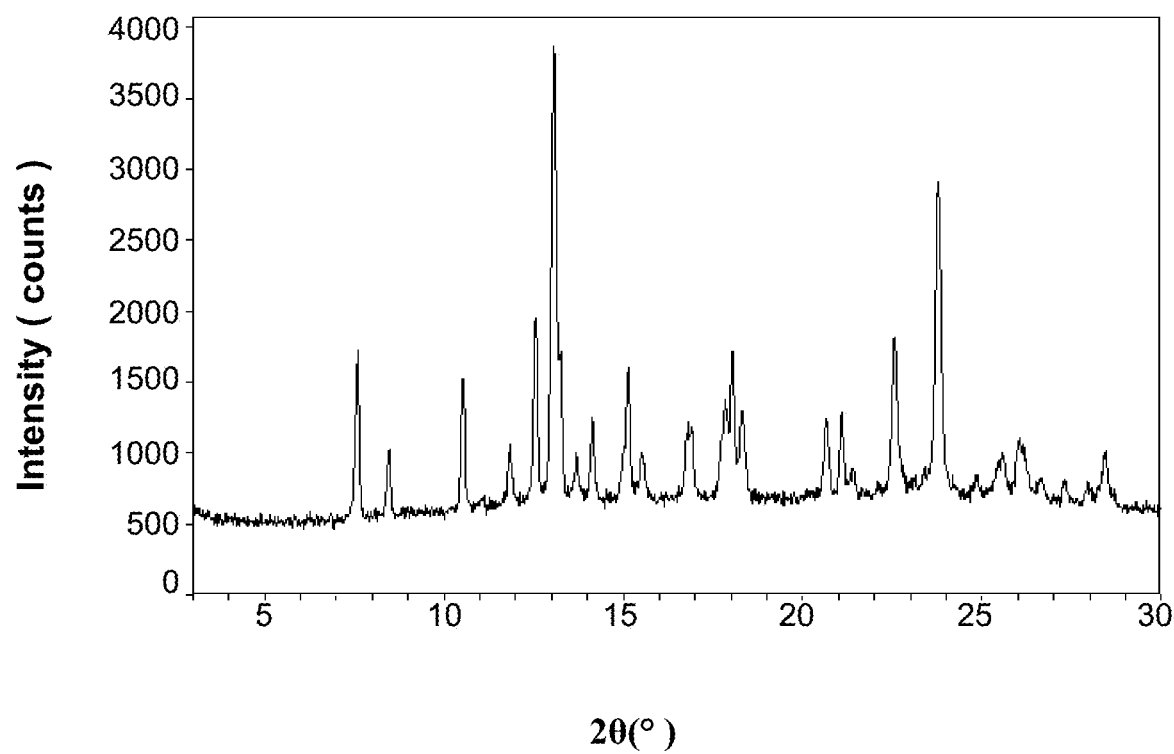
FIG. 13 is the XRPD pattern of ACP-196 Form 4 prepared according to Example 27 of the present invention.

Its XRPD pattern is shown in FIG. 13.

Example 28

| Component | Dosage (mg) |
|---|---|
| ACP-196 Form 1 (active ingredient basis)/Form 2 | 50 |
| Compressible starch | 110 |
| Cross-linked povidone | 5 |
| Microcrystalline cellulose | 80 |
| Silica | 5 |
| Total | 250 |

Mixed ACP-196 Form 1 or ACP-196 Form 2, compressible starch, microcrystalline cellulose and crosslinked polyvinyl ketone, then lubricated the mixture by silica, and then finally compressed into tablets.

Example 29

| Component | Dosage (mg) |
|---|---|
| ACP-196 Form 1 (active ingredient basis)/Form 2 | 100 |
| Ethyl cellulose | 100 |
| Hydroxypropylmethylcellulose | 10 |
| Lactose | 110 |
| Microcrystalline cellulose | 80 |
| Magnesium stearate | 5 |
| Talc | 5 |
| Total | 410 |

Mixed ACP-196 Form 1 or ACP-196 Form 2, ethyl cellulose, hydroxypropyl methyl cellulose, lactose and microcrystalline cellulose, granulated with 75% ethanol, dried, crushed, shifted through 80 mesh sieve, then added magnesium stearate and talc to mix evenly and filled into the capsule.

The described above are only specific embodiments for illustrating the present invention, but without limiting it to that. Any changes or alternations, without creative work, made by those skilled in the art within the technical scope disclosed by the present invention, should fall within the scope of the present invention. Therefore, the scope of protection of the present invention shall be subject to the scope of protection defined in the claims

The invention claimed is:

1. ACP-196 Form 2, having the chemical structure shown in formula (II) below,

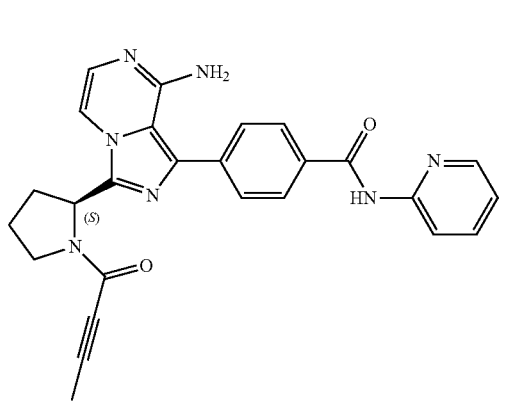

(II)

wherein, measured using Cu-Kα radiation, the X-ray powder diffraction pattern of the ACP-196 Form 2, expressed as 2θ angles, has the following characteristic peaks: 7.4±0.2°, 10.3±0.2°, 12.4±0.2°, 12.7±0.2°, 17.8±0.2° and 21.9±0.2°.

2. The ACP-196 Form 2 according to claim 1, wherein the X-ray powder diffraction pattern of the ACP-196 Form 2, expressed as 2θ angles, has the following characteristic peaks: 7.4±0.2°, 8.3±0.2°, 10.3±0.2°, 12.4±0.2°, 12.7±0.2°, 13.9±0.2°, 14.9±0.2°, 17.8±0.2°, 21.9±0.2°, 23.2±0.2°, 24.3±0.2° and 24.9±0.2°.

3. The ACP-196 Form 2 according to claim 2, wherein the X-ray powder diffraction pattern of the ACP-196 Form 2, expressed as 2θ angles, has the following characteristic peaks and relative intensities:

| Diffraction angel 2θ | Relative intensity % |
|---|---|
| 7.4 ± 0.2° | 22.7 |
| 8.3 ± 0.2° | 10.7 |
| 10.3 ± 0.2° | 40.2 |
| 12.4 ± 0.2° | 47.5 |
| 12.7 ± 0.2° | 100.0 |
| 13.1 ± 0.2° | 16.1 |
| 13.9 ± 0.2° | 21.9 |
| 14.5 ± 0.2° | 20.5 |
| 14.9 ± 0.2° | 26.5 |
| 17.8 ± 0.2° | 58.5 |
| 21.9 ± 0.2° | 36.8 |
| 23.2 ± 0.2° | 59.1 |
| 24.3 ± 0.2° | 31.6 |
| 24.9 ± 0.2° | 23.1 |
| 25.3 ± 0.2° | 19.3 |

4. A method of preparing the ACP-196 Form 2 according to claim 1, comprising any one of the following methods:
1) heating ACP-196 Form 1 to a temperature between 120° C. and 130° C., then cooling to room temperature to obtain the ACP-196 Form 2; wherein:
the heating rate is from 20° C/min to 50° C/min; and
the cooling rate is from 20° C/min to 40° C/min;
2) forming a suspension of ACP-196 solids in a solvent, adding seeds of the ACP-196 Form 2, stirring for crystallization and precipitation, then separating and drying to obtain the ACP-196 Form 2; wherein:
the solvent is selected from the group consisting of an alcohol, a ketone, an ester, tetrahydrofuran, 1,4-dioxane, acetonitrile and toluene;
the weight to volume ratio of ACP-196 solids to the solvent is from 150 mg/1 mL to 300 mg/1 mL;
the amount of seeds added is from 10% to 30%;
the stirring time is from 3 days to 7 days; and
the stirring is carried out at room temperature;
3) forming a solution of ACP-196 in a co-solvent, adding the solution to an anti-solvent containing the ACP-196 Form 2 solids, stirring for crystallization and precipitation, then separating and drying to obtain the ACP-196 Form 2; wherein:
the co-solvent is selected from the group consisting of an alcohol, a ketone, tetrahydrofuran, 1,4-dioxane and acetonitrile;
the weight to volume ratio of ACP-196 solids to the co-solvent is from 100 mg/1 mL to 200 mg/1 mL;
the anti-solvent is selected from the group consisting of an ether and an alkane;
the amount of seeds added is from 10% to 30%;
the stirring time is from 12 hours to 24 hours; and
the stirring for crystallization and precipitation is carried out at room temperature; or
4) forming a solution of ACP-196 solids in a solvent, cooling, adding seeds of the ACP-196 Form 2, stirring for crystallization and precipitation, and then separating and drying to obtain the ACP-196 Form 2; wherein:
the solvent is a mixture of two solvents selected from the group consisting of an alcohol, a ketone, an ester, an ether and an alkane;
the volume ratio of the two solvents in the solvent mixture is 1:1;
the weight to volume ratio of ACP-196 solids to the solvent is from 100 mg/1 mL to 200 mg/1 mL;
the temperature of forming the solution is from 60° C. to 80° C.;
the end point of cooling is from 10° C. to 30 C;
the amount of seeds added is from 20% to 30%;
the crystallization and precipitation temperature is room temperature, and the crystallization and precipitation time is from 2 days to 3 days.

5. A pharmaceutical composition comprising a therapeutically effective amount of the ACP-196 Form 2 according to claim 1, and at least one pharmaceutically acceptable carrier or additive.

6. The pharmaceutical composition according to claim 5, wherein the pharmaceutical composition is selected from suitable dosage forms for oral, sublingual, subcutaneous, intravenous, intramuscular, nasal, topical or rectal administration; or oral dosage forms of tablets, capsules, powders, granules, solutions or suspensions.

7. The method according to claim 4, wherein the anti-solvent is methyl tert-butyl ether.

* * * * *